United States Patent [19]

Cornils et al.

[11] 4,215,073

[45] Jul. 29, 1980

[54] PROCESS FOR THE PRODUCTION OF DIAMINES

[75] Inventors: Boy Cornils, Dinslaken; Werner Konkol, Oberhausen; Gerhard Diekhaus, Oberhausen; Ernst Wiebus, Oberhausen, all of Fed. Rep. of Germany

[73] Assignee: Ruhrchemie Aktiengesellschaft, Oberhausen, Fed. Rep. of Germany

[21] Appl. No.: 43,949

[22] Filed: May 30, 1979

[30] Foreign Application Priority Data

Jun. 3, 1978 [DE] Fed. Rep. of Germany ....... 2824423

[51] Int. Cl.² .............................................. C07C 85/08
[52] U.S. Cl. ............................ 260/563 D; 260/583 P
[58] Field of Search ....................... 260/583 P, 563 D

[56] References Cited

U.S. PATENT DOCUMENTS

| 2,636,051 | 4/1953 | Whetstone et al. | 260/583 P |
| 4,160,785 | 7/1979 | Webb et al. | 260/583 P |

*Primary Examiner*—John Doll
*Attorney, Agent, or Firm*—Sprung, Felfe, Horn, Lynch & Kramer

[57] ABSTRACT

A two-step process for the production of aliphatic or cycloaliphatic diamines having 4 to 18 carbon atoms is disclosed wherein in the first step an aliphatic or cycloaliphatic dialdehyde is reacted with a monoamine olefin at atmospheric pressure at a temperature up to 100° C. to form the corresponding diazomethyne and in the second step the diazomethyne is reacted at 60° to 200° C. and 50 to 300 bar with a mixture of ammonia and hydrogen in the presence of a hydrogenation catalyst to form the corresponding diamine and release of monoamine.

8 Claims, No Drawings

PROCESS FOR THE PRODUCTION OF DIAMINES

BACKGROUND OF THE INVENTION

1. Field of the Invention

This invention relates to a production of aliphatic and cycloaliphatic diamines. More especially, this invention relates to a two-step process for the production of aliphatic and cycloaliphatic diamines by reaction of dialdehydes with a monoamine to form the corresponding diazomethyne and subsequent reaction of the so-formed diazomethyne with ammonia and hydrogen in the presence of a hydrogenation catalyst (aminating hydrogenation).

2. Discussion of the Prior Art

Diamines, especially $\alpha,\omega$-alkylene diamines, for example, hexamethylene diamine and also cycloaliphatic diamines such as 1,4-diaminocyclohexane are valuable intermediate products for a great number of chemical syntheses. They find use in the production of polyamides or of polyurethanes as well as curing agent component for epoxide resins.

Aliphatic or cycloaliphatic diamines may be produced by hydrogenation of the corresponding dinitriles. However, since the production of the dinitriles is commercially expensive, this method permits the economic preparation of diamines only in exceptional cases.

Another mode of operation for the production of diamines starts from dialcohols which are reacted with ammonia. Since the reaction requires high temperatures which favor the formation of by-products, the yield is only low.

Instead of reacting dialcohols with ammonia, it is further known to react dialdehydes in the presence of catalysts with ammonia and hydrogen in one step. However, the achievable yields are unsatisfactory also in this process because the aldehydes enter into addition and condensation reactions and polyimines are formed.

Therefore, due to the great importance of the diamines, there was the problem to develop a process which permits the production of this class of compounds in a high yield and with a technically justifiable expense.

SUMMARY OF THE INVENTION

It has now been found surprisingly that the production of aliphatic or cycloaliphatic diamines containing 4 to 18 carbon atoms is sucessfully achieved by contacting an aliphatic or cycloaliphatic dialdehyde in a first stage at atmospheric pressure and at a temperature up to 100° C. with a monoamine to form the corresponding diazomethyne and contacting the latter, in a later reaction stage, at 60° to 200° C. and 50 to 300 bars, with ammonia and hydrogen in the presence of a hydrogenation catalyst into a diamine while the monoamine is split off. Preferably, this later stage is performed at 60° to 160° C. and 50 to 250 bars.

The process according to the invention permits the production of diamines from dialdehydes in yields which exceed 95%. It could not be predicted that if the reaction is carried out in two stages, the polymerization, aldolization or condensation of the aldehydes which are responsible for considerable losses in yield are suppressed almost completely.

The new method of operation is suitable for the production of aliphatic and cycloaliphatic diamines especially hydrocarbon, e.g., alkyl and cycloalkyl diamines 4 to 18 carbon atoms, e.g., 1,6-hexamethylene-diamine, 1,8-octamethylene diamine, 1,12-dodecamethylene diamine, and the isomeric bis (aminomethyl)-tricyclo[5.2.1.0$^{2.6}$]-decanes.

Aliphatic or cycloaliphatic, e.g., alkyl and cycloalkyl dialdehydes are used as starting materials. The position of the two carbonyl groups to each other is optional, preferred aliphatic dialdehydes being $\alpha,\omega$-compounds. Examples of dialdehydes which can be reacted by the process according to the invention include dialdehydes of dialkanols which dialdehydes include 1,4-butanedial, 1,6-hexanedial, 1,2-dodecanedial, bisformyltricyclo[5.2.1.0$^{2.6}$]-decane. The dialdehydes are produced by known processes, for example, from diolefins by hydroformylation, i.e. reaction with a mixture of hydrogen and carbon monoxide in the presence of suitable catalysts such as rhodium or cobalt in finely divided form or compounds of rhodium or cobalt.

Straight-chain or branched-chain aliphatic, e.g., alkyl monoamines having 3 to 18 carbon atoms are used for the reaction of dialdehydes in the first reaction stage. For example, alkyl amines such as n-propylamine, i-propylamine, n-butylamine, sec. butylamine, tert-butylamine, the isomeric pentylamines, hexylamine as well as 2-ethylhexylamine, i-tridecylamine, i-octadecylamine are suitable. The reaction is carried out without the use of pressure at temperatures of 10° to 100° C. The reaction temperature is selected in accordance with the boiling behavior of the reactants. Desirably an excess of 10 to 100 mol percent of the monoamine is used and the dialdehyde is added portionwise to the amine. The use of at least 2.4 mols of monoamine per mole of dialdehyde has been found to be useful. The presence of a solvent for the reactants and/or the reaction product is not absolutely necessary but may be desirable in special cases. Aliphatic or aromatic hydrocarbons such as toluene, xylene are then preferably used as reaction medium.

The diazomethyne formed in the first reaction stage is subjected to an aminating hydrogenation in the presence of catalysts without separation from the accompanying reactants and by-products and without previous purification.

The usual hydrogenation catalysts are suitable for the aminating hydrogenation among which are catalysts which contain one or more elements of Group VIII of the Periodic Table as metal and/or oxide. The active component of the catalyst may be used alone or in combination with a support. Examples of suitable supports include alumina, kieselguhr, silicic acid and silicates, especially aluminum silicates. Examples of catalysts which are suitable for use in the process according to the invention include nickel, cobalt, rhodium or platinum catalysts prepared by precipitation or impregnation such as nickel or cobalt on alumina having a nickel or cobalt content up to 75% by weight. Advantageously, the last-mentioned catalysts contain magnesium, manganese and/or chromium in the form of their compounds as promoters.

The hydrogenation may be carried out with a suspended catalyst or fixed bed catalyst in both the liquid phase and gas phase. It is carried out in the presence of at least 2 mols and preferably 4 to 20 mols of ammonia and 1 to 4 mols of hydrogen per mol of diazomethyne. The presence of a solvent such as alcohols, ethers or hydrocarbons is possible but not mandatory. The reaction temperature is 60° to 200° C. and the total pressure 50 to 300 bars. To maintain the pressure desired, hydrogen is continuously supplied to the reaction mixture.

The reaction may be carried out in reactors of conventional construction. For example, tubular reactors are suitable for carrying out the first reaction stage, but stirred vessels may also be used. The aminating hydrogenation is carried out in autoclaves and preferably in tubular reactors.

During the aminating hydrogenation in the second synthesis stage, the monoamine fed into the first synthesis stage is re-formed. It is produced thereby in an amount sufficient to cover the monoamine requirement of the first reaction stage. Therefore, both synthesis stages are preferably carried out continuously with recycling of the monoamine formed in the second reaction stage into the first reaction stage.

In order to more fully illustrate the nature of the invention and a manner of practicing the same, the following Comparative Example and Example are presented. The Comparative Example shows the poor yield of diamine derived by aminating hydrogenation of a dialdehyde. When comparing the Comparative Example with the Example, it is evident that an improved yield on the basis of the amount of dialdehyde charged is obtained in that in accordance with the procedure of the invention a 95% of theory yield of amine is realized versus a 44% yield when the dialdehyde is reacted directly with ammonia and hydrogen.

COMPARATIVE EXAMPLE

3(4),8(9)-Bisformyl-triclo[5.2.1.0$^{2.6}$]-decane mixed with 1% by weight of a finely divided catalyst containing about 55% of nickel in addition to 4 to 6% of magnesia as activator and 30 to 35% of silicic acid-containing carrier material is pumped with a throughput of 0.27 V/V/h into the bottom of a vertical high pressure tube having a capacity of 2 parts by volume. At the same time, 10 mols of ammonia are fed per mol of dialdehyde. At 140° C. and a total pressure maintained at 80 bar by continuously introducing hydrogen, the reaction product leaving the reactor at the top and calculated free from water, ammonia and catalyst contains about 10% of 3(4)-aminomethyltricylco [2.5.1.0$^{2.6}$]-decane, 35% of 3(4),4(9)-bis-(amonomethyl)-tricyclo[5.2.1.0$^{2.6}$]-decane, 5% of 3(4)-hydroxymethyl-8(9)-aminomethyltricyclo[5.2.1.0$^{2.6}$]-decane and 50% of higher boiling point materials.

The yield of 3(4),8(9)-bis-(aminomethyl)-tricyclo-[5.2.1.0$^{2.6}$]-decane is about 44% of the theory, based on the dialdehyde charged.

EXAMPLE

A diazomethyne obtained by reaction of 3(4),8(9)-bisformyltricycle[5.2.1.0$^{2.6}$]-decane and n-butylamine (100% excess) and mixed with 1% by weight of the catalyst described in the Comparative Example is pumped at a throughput rate of 0.27 V/V/h into the reactor described in the Comparative Example. At the same time, 10 mols of ammonia are fed per one mol diazomethyne. At 140° C. and a total pressure maintained at 80 bars by continuously introducing hydrogen, the reaction mixture leaving the reactor at the top has the following product composition, calculated free from water, ammonia and catalyst:

| | |
|---|---|
| n-Butylamine | 59.3% |
| 3(4)-aminomethyltricyclo[5.2.1.0$^{2.6}$]-decane | 2.8% |
| 3(4),8(9)-bis-(aminomethyl)tricyclo[5.2.1.0$^{2.6}$]-decane | 34.3% |
| 3(4)-hydroxymethyl-8(9)-aminomethyltricyclo-[5.2.1.0$^{2.6}$]-decane | 1.4% |
| Higher boiling point materials | 2.2% |

The amount produced of n-butylamine covers the requirement which, based on unit time, is necessary for the production of the diazomethyne.

The yield of 3(4),8(9)-bis-(aminomethyl)tricyclo-[5.2.1.0$^{2.6}$]-decane is about 95% of the theory, based on the amount of dialdehyde charged.

What is claimed is:

1. A process for the production of an aliphatic or cycloaliphatic diamine having 4 to 18 carbon atoms which comprises the steps of:
    A. in a first stage contacting an aliphatic or cycloaliphatic dialdehyde with a monoamine at atmospheric pressure and at a temperature up to 100° C. to form the corresponding diazomethyne; and
    B. in a subsequent stage contacting said diazomethyne with a mixture of ammonia and hydrogen at a temperature of 60° to 200° C. and at a pressure of 50 to 300 bars in the presence of a hydrogenation catalyst.
2. A process according to claim 1 wherein said monoamine has 3 to 18 carbon atoms.
3. A process according to claim 1 wherein said monoamine is employed in a 10 to 100 mol stoichiometric excess based upon the amount of dialdehyde.
4. A process according to claim 1 wherein said dialdehyde is added portionwise to said monoamine.
5. A process according to claim 1 wherein the hydrogenation catalyst is nickel or cobalt containing catalyst.
6. A process according to claim 1 wherein in the hydrogenation of the diazomethyne 4 to 20 moles of ammonia are employed per mol of diazomethyne.
7. A process according to claim 1 wherein the reaction of the diazomethyne is carried out at 60° to 160° C. and 50 to 250 bar.
8. A process according to claim 1 wherein the formation of the diazomethyne and the subsequent hydrogenation thereof in the presence of ammonia are carried out continuously while recycling monoamine produced as a result of the hydrogenation.

* * * * *